(12) United States Patent
Logan et al.

(10) Patent No.: US 7,891,311 B2
(45) Date of Patent: Feb. 22, 2011

(54) FLUID FLOW INDICATOR

(75) Inventors: Kenneth Arthur Logan, Callaghan (AU); Paul Christopher Dastoor, Callaghan (AU); Ian Wesley Robert Clarke, Callaghan (AU); Peter J. Hester, Revesby (AU)

(73) Assignee: Keystone Medical Pty Ltd, Morisset, New South Wales (AU)

( * ) Notice: Subject to any disclaimer, the term of this patent is extended or adjusted under 35 U.S.C. 154(b) by 0 days.

(21) Appl. No.: 12/224,581

(22) PCT Filed: Mar. 2, 2007

(86) PCT No.: PCT/AU2007/000266

§ 371 (c)(1), (2), (4) Date: Aug. 29, 2008

(87) PCT Pub. No.: WO2007/098565

PCT Pub. Date: Sep. 7, 2007

(65) Prior Publication Data

US 2009/0025626 A1    Jan. 29, 2009

(30) Foreign Application Priority Data

Mar. 3, 2006    (AU) .............................. 2006901092

(51) Int. Cl.
*G01F 15/16* (2006.01)
*A61M 5/14* (2006.01)

(52) U.S. Cl. ....................................... 116/273; 116/270

(58) Field of Classification Search ................. 116/246, 116/266, 270, 272, 273, 274, 275, 276, DIG. 7, 116/DIG. 25, DIG. 42
See application file for complete search history.

(56) References Cited

U.S. PATENT DOCUMENTS 1,910,752 A * 5/1933 Coles ......................... 116/273
2,136,261 A * 11/1938 Anderson ..................... 73/861

(Continued)

FOREIGN PATENT DOCUMENTS

FI        102568 B    * 12/1998

(Continued)

*Primary Examiner*—R. A. Smith
(74) *Attorney, Agent, or Firm*—Harness, Dickey & Pierce, P.L.C.

(57) ABSTRACT

A fluid flow indicator for observation of low flow rates in liquids includes a capillary tube (12) slidably mounted at each end in passageways (4) and (5) and biased into a no-flow indicating position by a castellated elastomeric membrane (14) providing a sealed barrier within a chamber (1) between a first zone (17) and a second zone (18). Fluid flow introduced through spigot (9) causes the capillary tube (12) to slide to the opposite end of the passageways (4) and (5) whereupon the deformed position of the elastomeric membrane (14) can readily be observed through transparent walls (3) in the chamber (1). Upon cessation of flow, the elastomeric membrane (14) causes the capillary tube (12) to revert to its original position.

20 Claims, 1 Drawing Sheet

U.S. PATENT DOCUMENTS

| | | | |
|---|---|---|---|
| 2,137,102 A * | 11/1938 | Terrell, Jr | 73/861 |
| 2,662,502 A * | 12/1953 | Turner | 116/273 |
| 3,126,739 A * | 3/1964 | Whitehill | 73/861.47 |
| 3,633,612 A * | 1/1972 | Gross | 137/498 |
| 4,592,747 A * | 6/1986 | Pool | 604/246 |
| 4,601,700 A | 7/1986 | Thompson et al. | |
| 4,790,811 A * | 12/1988 | Bloxom, Jr. | 604/27 |
| 4,819,577 A * | 4/1989 | Campau | 116/264 |
| 5,645,011 A | 7/1997 | Winkler et al. | |
| 5,798,697 A * | 8/1998 | Wiseman | 340/610 |
| 5,829,093 A * | 11/1998 | Kim | 15/339 |
| 5,845,597 A * | 12/1998 | Karpal | 116/268 |
| 6,645,175 B2 | 11/2003 | Kriesel et al. | |
| 7,013,726 B1 * | 3/2006 | Drummond et al. | 73/276 |
| 7,159,533 B1 * | 1/2007 | Redd et al. | 116/274 |
| 2005/0011282 A1* | 1/2005 | Voege et al. | 73/861.44 |
| 2008/0262441 A1* | 10/2008 | Walborn et al. | 604/247 |

FOREIGN PATENT DOCUMENTS

| | | |
|---|---|---|
| JP | 03172766 A * | 7/1991 |
| WO | WO-2006/079067 A1 | 7/2006 |

* cited by examiner

FLUID FLOW INDICATOR

FIELD OF THE INVENTION

This invention relates to a fluid flow indicator and has been devised particularly though not solely for indicating the presence of flow in a low flow rate medical infusion device.

BACKGROUND OF THE INVENTION

There are many devices where it is desired to dispense a fluid, and typically a liquid, at a low flow rate, and where it is often difficult to determine whether or not flow is occurring in a delivery conduit. Many of these applications are in the medical arena typified by the liquid dispenser described in our own International Patent Application PCT/AU02/01499 which supplies fluid for medical infusion at controlled low flow rates.

In such situations, it is important for the patient or the carer to be able to determine that flow has been established initially, and is continuing over the desired period of treatment. This has been difficult to establish in the past, particularly in low cost "disposable" types of apparatus and it has been common for patients or carers to simply revert to an observation of the amount of fluid contained in the supply reservoir from time to time to check that flow delivery is occurring. In most instances it would take several hours to observe a discernable change in the volume, in other instances it is not possible at all. In many instances this is quite unsatisfactory as the observations are difficult, and can result in heightened anxiety for the patient or the carer, and in extreme situations medical complications arising from a lack of flow over a period of time until the situation is able to be determined.

It is also desirable in such devices to provide a flow regulator which will deliver the fluid at a controlled predetermined flow rate without complication or the necessity to set parameters by the patient or carer.

There are many other applications, including non-medical applications such as the delivery of lubricating fluids to machinery or the dosing of small amounts of chemicals, where it is desirable to be able to monitor the fact that low flow rates are occurring by simple observation, and by the provision of inexpensive flow monitoring equipment.

SUMMARY OF THE INVENTION

Accordingly, in its broadest aspect the present invention provides a fluid flow indicator including a chamber through which flow is directed, a fluid flow restricting element arranged to be mobile within the chamber in the direction of flow, means to direct fluid flow through the fluid flow restricting element, an elastic medium biasing the fluid flow restricting element to a neutral position when there is no flow therethrough, and an observation means arranged to observe movement of the flow restricting element from the neutral position when fluid flow is occurring within the chamber.

Preferably the fluid flow restricting element comprises a capillary tube.

Preferably the capillary tube comprises a glass capillary tube.

Alternatively the fluid flow restricting element comprises a porous membrane.

Typically the elastic medium comprises an elastomeric polymer or alternatively thin plastic materials, springs, or other known elastic devices.

Although the flow restricting element and the elastic medium may be separate materials, it is possible for them to be combined, for example as an elastomeric membrane of porous material, or incorporating a porous component.

In a further aspect the present invention provides a fluid flow indicator including a capillary tube having a small central bore through which restricted flow is delivered in use, a fluid chamber incorporating first and second aligned passageways at opposite ends of the chamber sized to receive and support each end of the capillary tube in such a manner that the capillary tube is free to move axially back and forth over a limited range of travel, an elastomeric membrane having a central portion sealed to the capillary tube at an intermediate location along the capillary tube and a peripheral portion sealed to the periphery of the chamber at a location between the aligned passageways, dividing the chamber into first and second zones, such that when a fluid supply conduit is coupled to the first passageway fluid passes in use into the central bore in the capillary tube and also into the first zone of the chamber, the restricted flow through the small central bore causing the rate of flow of fluid therethrough to be regulated and back pressure to build up in the first zone of the chamber where it impinges against the elastomeric membrane causing the membrane and the attached capillary tube to move from a first position to a second position indicating that flow is occurring within the capillary tube.

Preferably, when flow ceases through the central bore in the capillary tube, pressure equalizes in the first and second zones of the chamber and the elastomeric nature of the membrane moves the attached capillary tube back from the second position to the first position indicating that flow is no longer occurring.

Preferably, flow is delivered from the capillary tube via the second aligned passageway to a flow discharge conduit.

Preferably, the first and second aligned passageways incorporate stop means arranged to limit the extremes of axial travel of a capillary tube within the passageways.

Preferably, the stop means comprise shoulders within the first and second aligned passageways.

Preferably, the chamber is cylindrical in configuration with the first and second passageways aligned with the axis of the cylindrical chamber and the elastomeric membrane being substantially circular in configuration.

Preferably, the elastomeric membrane is castellated in cross-section, incorporating a plurality of concentric castellations.

Preferably, the cylindrical chamber is formed in two sections, joined at/or about the circumference of the mid-point of the chamber, and wherein the outer periphery of the membrane is engaged with and sealed to the periphery of the chamber at the join between the two sections.

Preferably, the membrane is clamped within the join and the two sections of the chamber ultrasonically welded together.

Preferably, at least one section of the chamber is formed from a transparent or translucent material enabling the position of the membrane to be observed from outside the chamber.

Alternatively, the chamber incorporates sensing means arranged to detect the position of the membrane or the capillary tube within the chamber and convey that position to an observer. The sensing means could be electrical, optical, magnetic or any other means of detecting deflection of the membrane.

BRIEF DESCRIPTION OF THE DRAWINGS

Notwithstanding any other forms that may fall within its scope, one preferred form of the invention will now be described by way of example only with reference to the accompanying drawings in which.

DETAILED DESCRIPTION OF THE INVENTION

Figure 1:
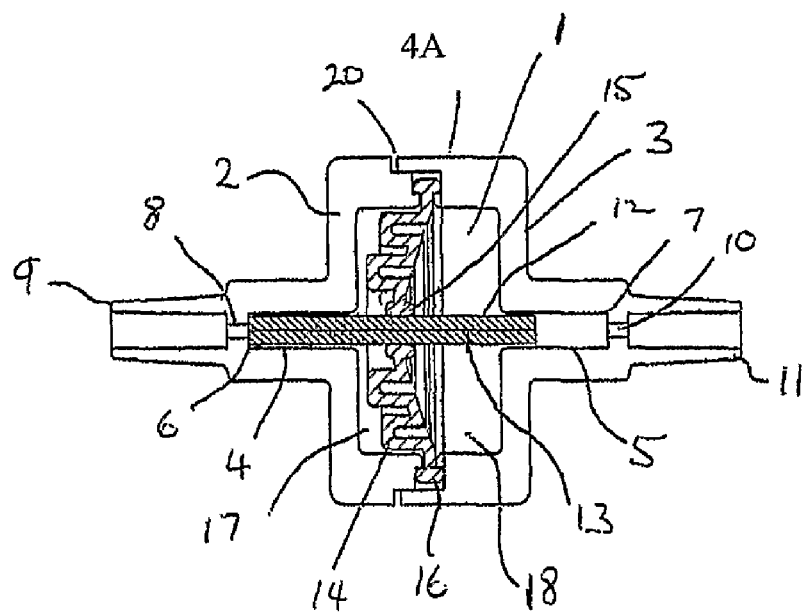
FIG. 1 is a cross-sectional elevation through a fluid flow indicating device according to the invention.

The preferred form of the invention will be described as an embodiment particularly suitable for use for medical infusion devices such as "intravenous drips" where it is necessary to monitor very low flow rates through a flexible supply tube. It will be appreciated however that the device may take many other forms and be used in many other different applications including non-medical uses such as the delivery of lubricating fluids to machinery or the dosing of small amounts of chemicals into fluid flows.

The fluid flow indicator is typically manufactured from plastics materials which may be formed by injection moulding to define a chamber 1 which is substantially cylindrical in configuration having circular end walls 2 and 3 and a drum-like peripheral wall 4A.

The chamber incorporates first and second aligned passageways 4 and 5 respectively which are aligned with the axis of the cylindrical chamber 1 and are provided with stop means typically in the form of shoulders 6 and 7 at or toward the ends of the passageways 4 and 5.

The passageway 4 communicates by way of an opening 8 with a supply spigot 9 to which may be attached a fluid supply hose in use, and similarly the passageway 5 communicates via opening 10 with a delivery spigot 11 which may be connected to a delivery hose in use.

Figure 2:
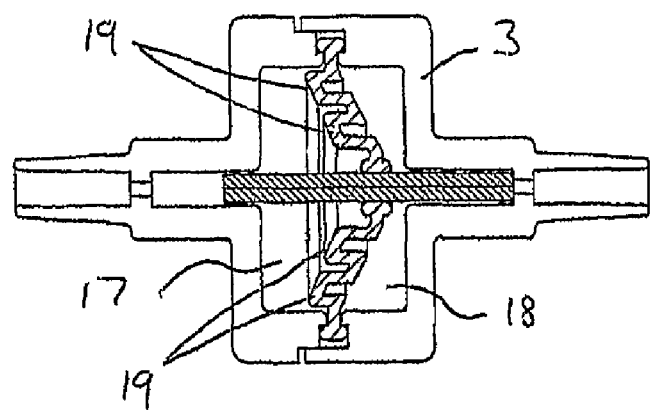
FIG. 2 is a similar view to FIG. 1 showing the position of the membrane and capillary tube within the device when fluid flow is occurring.

A capillary tube 12 having a small central bore 13 typically approximately 0.05 millimeter internal diameter is provided, located and supported at each end within the first and second aligned passageways 4 and 5 in such a manner that the capillary tube is free to move axially back and forth over a limited range of travel between the position shown in FIG. 1 and the position shown in FIG. 2. The limits of travel are determined by the shoulders 6 and 7 in the passageways 4 and 5 respectively.

The fluid flow indicator is further provided with an elastomeric membrane 14 having a central portion 15 sealed to the capillary tube 12 at an intermediate location along the capillary tube, and a peripheral portion 16 sealed to the periphery 4 of the chamber 1 at a location between the aligned passageways so as to divide the chamber into a first zone 17 and a second zone 18.

The elastomeric membrane 14 is designed with a "memory" or flex characteristics such that it imparts a biasing motion to the capillary tube 12 tending to move the tube 12 into a "no-flow" position as shown in FIG. 1. This may be achieved in a number of ways but has been found most beneficially effected by forming the elastomeric membrane with concentric castellations 19 (FIG. 2) to impart the necessary degree of spring action.

In use, a supply of fluid is connected to the inlet spigot 9 and fluid supplied through the opening 8 into the first passageway 4. Fluid moves from the first passageway 4 into the first zone 17 of chamber 1 and also through the small central bore 13 in the capillary tube 12. Due to the restrictive nature of the small bore in the capillary tube, back pressure builds up on the supply side of the device causing an increase in pressure in the first zone 17 of the chamber 1 where it impinges against the elastomeric membrane 14 causing the membrane and the attached capillary tube to move from a first position as shown in FIG. 1 to a second position as shown in FIG. 2 indicating that flow is occurring within the capillary tube.

Over time, fluid also builds up in the second zone 18 of the chamber 1 as it issues from the down stream end of the capillary tube into the second aligned passageway 5 from where it can flow into the second zone 18 of chamber 1. Under flow conditions however the pressure in the first zone 17 is always greater than the pressure in the second zone 18 due to the restricted nature of flow through the small bore 13 in the capillary tube 12 causing back pressure to build up in the first zone 17. While flow is maintained, the greater pressure in the first zone 17 causes the elastomeric membrane to be deformed into the position shown in FIG. 2 which is an indication that flow is present.

Should flow cease, the pressure will equalize between the first and second zones 17 and 18 whereupon the elastomeric nature and configuration of the membrane 14 will bias the capillary tube back into the position shown in FIG. 1 indicating that flow has ceased.

The most convenient way of observing the position of the elastomeric membrane 14, and hence whether flow is occurring or not, is to make at least one of the portions 2 and 3 of the chamber housing transparent or translucent so that the position of the membrane can be observed through the chamber wall. It has been found in use, that it is most effective to make only one half of the chamber transparent, and for the membrane to be provided in a bright colour so that it is easy to observe when the membrane has moved into the position shown in FIG. 2, particularly if the portion 3 has been made transparent.

The device may be constructed in any convenient manner, but it has been found effective to mold the two halves of the chamber as shown in the attached drawings with a join line at 20 and to wedge the outer periphery 16 of the elastomeric membrane into the join between the two halves 2 and 3 as the housing is assembled. The housing may then be ultrasonically welded together to complete the assembly of the fluid flow indicator.

In this manner it is possible to provide a fluid flow indicator that is simple and inexpensive to manufacture and yet which is reliable in use and simple for an unskilled observer to note whether flow is occurring or not in the supply and delivery tubes connected to the inlet and outlet spigots 9 and 11. This has particular application in medical infusion devices but can also be applied to other medical and non-medical situations as previously referred to above.

Although the device has been described as indicating flow by a simple visual observation, it will be appreciated that other forms of output may be applied to enable the user to determine the position of the elastomeric membrane 14. For example, the housing may be completely opaque, and a sensor, either electronic or mechanical, used to indicate the position of the membrane within the housing and therefore whether flow is occurring or not.

It should also be recognised that although the preferred configuration has been described utilising a capillary tube located in the centre of an elastomeric membrane this is not the only configuration capable of the broader invention. For example, in alternative configurations the membrane could be replaced by a plug or piston, the elastic nature of the membrane could be replaced by a spring, the micro-bore capillary tube restrictor could be replaced by an alternative channel or series of micro-bore holes, the single membrane could be replaced by multiple membranes, or other means of causing the flow to channel from a high pressure (small bore) to a low pressure (larger bore) while moving an attached marker, could be provided.

The device also has the inherent advantage of not only indicating whether flow is occurring but in accurately controlling the rate of flow by predetermining the size of the small central bore 13 through the capillary tube 12. This has the advantage of simplicity and low cost, particularly applicable to low cost disposable medical infusion applications.

The invention claimed is:

1. A fluid flow indicator including a chamber through which flow is directed, a fluid flow restricting element arranged to be mobile within the chamber in the direction of flow, means to direct fluid flow through the fluid flow restricting element, an elastic medium biasing the fluid flow restricting element to a neutral position when there is no flow therethrough, and an observation means arranged to allow a user to directly observe movement of the flow restricting element from the neutral position to a displaced position when fluid flow is occurring within the chamber.

2. The fluid flow indicator as claimed in claim 1 wherein the fluid flow restricting element comprises a capillary tube.

3. The fluid flow indicator as claimed in claim 1 wherein the fluid flow restricting element comprises a porous membrane.

4. The fluid flow indicator as claimed in claim 1 wherein the elastic medium comprises an elastomeric polymer.

5. The fluid flow indicator as claimed in claim 1 wherein the elastic medium comprises a spring.

6. The fluid flow indicator as claimed in claim 1 wherein the flow restricting element and the elastic medium are combined as an elastomeric membrane of porous material.

7. The fluid flow indicator of claim 1 wherein the fluid flow restricting element has a peripheral portion that is coupled to the chamber.

8. The fluid indicator of claim 7 wherein the fluid flow restricting element includes concentric castellations formed within the peripheral portion.

9. The fluid flow indicator of claim 8 wherein an innermost concentric castellation is located intermediate an inlet of the chamber and a plane defined by the peripheral portion in the neutral position and located intermediate an outlet of the chamber and the plane defined by the peripheral portion in the displaced position.

10. The fluid flow indicator of claim 1 wherein the chamber is substantially cylindrical and includes first and second circular end walls, at least one of the first and second end walls being formed of a transparent or translucent material enabling the position of the membrane to be observed from outside the chamber.

11. The fluid flow indicator of claim 10 wherein the other of the first and second circular end walls is non-transparent and wherein the neutral position corresponds to the fluid flow restricting element being positioned substantially within the non-transparent end wall and the displaced position corresponds to the fluid flow restricting element being positioned substantially within the transparent or translucent end wall.

12. A fluid flow indicator including a capillary tube having a small central bore through which restricted flow is delivered in use, a fluid chamber incorporating first and second aligned passageways at opposite ends of the chamber sized to receive and support each end of the capillary tube in such a manner that the capillary tube is free to move axially back and forth over a limited range of travel, an elastomeric membrane having a central portion sealed to the capillary tube at an intermediate location along the capillary tube and a peripheral portion sealed to the periphery of the chamber at a location between the aligned passageways, dividing the chamber into first and second zones, such that when a fluid supply conduit is coupled to the first passageway fluid passes in use into the central bore in the capillary tube and also into the first zone of the chamber, the restricted flow through the small central bore causing the rate of flow of fluid therethrough to be regulated and back pressure to build up in the first zone of the chamber where it impinges against the elastomeric membrane causing the membrane and the attached capillary tube to move from a first position to a second position indicating that flow is occurring within the capillary tube.

13. The fluid flow indicator as claimed in claim 12 arranged such that when flow ceases through the central bore in the capillary tube, pressure equalizes in the first and second zones of the chamber and the elastomeric nature of the membrane moves the attached capillary tube back from the second position to the first position indicating that flow is no longer occurring.

14. The fluid flow indicator as claimed in claim 12 wherein flow is delivered from the capillary tube via the second aligned passageway to a flow discharge conduit.

15. The fluid flow indicator as claimed in claim 12 wherein the first and second aligned passageways incorporate stop means arranged to limit the extremes of axial travel of a capillary tube within the passageways.

16. The fluid flow indicator as claimed in claim 12 wherein the elastomeric membrane is castellated in cross-section, incorporating a plurality of concentric castellations.

17. The fluid flow indicator as claimed in claim 12 wherein at least one section of the chamber is formed from a transparent or translucent material enabling the position of the membrane to be observed from outside the chamber.

18. A fluid flow indicator including a chamber through which flow is directed, a fluid flow restricting element comprising a capillary tube that is arranged to be mobile within the chamber in the direction of flow, means to direct flow through the fluid flow restricting element, an elastic medium biasing the fluid flow restricting element to a neutral position when there is no flow therethrough, and an observation means arranged to observe movement of the flow restricting element from the neutral position when fluid flow is occurring within the chamber.

19. The fluid flow indicator as claimed in claim 18 wherein the elastic medium comprises an elastomeric polymer.

20. The fluid flow indicator as claimed in claim 18 wherein the elastic medium comprises a spring.

\* \* \* \* \*